(12) United States Patent
Ben Noon et al.

(10) Patent No.: US 12,097,185 B2
(45) Date of Patent: Sep. 24, 2024

(54) COMPOSITIONS COMPRISING CIPROFLOXACIN AND CELECOXIB

(71) Applicant: Neurosense Therapeutics Ltd., Hertzliya (IL)

(72) Inventors: Alon Ben Noon, Ramat-Hasharon (IL); Jeffrey Sterling, Tel Mond (IL); Oron Yacoby-Zeevi, Karmei Yossef (IL); Sharon Cohen Vered, Kfar Saba (IL)

(73) Assignee: NEUROSENSE THERAPEUTICS LTD., Hertzliya (IL)

( * ) Notice: Subject to any disclaimer, the term of this patent is extended or adjusted under 35 U.S.C. 154(b) by 45 days.

(21) Appl. No.: 18/047,289

(22) Filed: Oct. 18, 2022

(65) Prior Publication Data

US 2023/0120880 A1    Apr. 20, 2023

Related U.S. Application Data

(60) Provisional application No. 63/257,130, filed on Oct. 19, 2021.

(51) Int. Cl.
*A61K 31/415* (2006.01)
*A61K 9/20* (2006.01)
*A61K 31/496* (2006.01)

(52) U.S. Cl.
CPC .......... *A61K 31/415* (2013.01); *A61K 9/2054* (2013.01); *A61K 31/496* (2013.01)

(58) Field of Classification Search
CPC .................................................. A61K 9/2054
See application file for complete search history.

(56) References Cited

U.S. PATENT DOCUMENTS 10,980,780 B2    4/2021    Ben-Noon

FOREIGN PATENT DOCUMENTS

WO    WO-2018235082 A1 *  12/2018    ........... A61K 31/415

OTHER PUBLICATIONS

Chaerunisaa A. et al.: "Release Adjustment of Two Drugs with Different Solubility Combined in a Matrix Tablet", AAPS PharmSciTech, vol. 20, No. 4, p. 1-8, Mar. 14, 2019 (Mar. 14, 2019).
Tiwari S. B. et al.: "Extended-Release Oral Drug Delivery Technologies: Monolithic Matrix Systems", Methods Mol. Biol., vol. 437, p. 217-243, Dec. 31, 2008 (Dec. 31, 2008).
Chakraborty S. et al.: "Effects of drug solubility on the release kinetics of water soluble and insoluble drugs from HPMC based matrix formulations",Acta. Pharm., vol. 59, No. 3, p. 313-323, Oct. 9, 2009 (Oct. 9, 2009).

* cited by examiner

*Primary Examiner* — John S Kenyon
(74) *Attorney, Agent, or Firm* — JMB Davis Ben-David (57) ABSTRACT

Embodiments relate to a tablet comprising celecoxib and ciprofloxacin or a pharmaceutically acceptable salt thereof, and low viscosity hydroxypropyl methylcellulose having a viscosity of less than 150 cP, when measured as a 2% solution in water at 20° C.

20 Claims, 1 Drawing Sheet

COMPOSITIONS COMPRISING CIPROFLOXACIN AND CELECOXIB

CROSS REFERENCE TO RELATED APPLICATIONS

Benefit is claimed to U.S. Provisional Patent Application No. 63/257,130 filed Oct. 19, 2021; the contents of which are incorporated by reference herein in its entirety.

FIELD

Provided herein are dosage forms comprising a ciprofloxacin or pharmaceutically acceptable salt thereof, and celecoxib.

BACKGROUND

Ciprofloxacin is an antibiotic which has been marketed in many countries for treatment of various bacterial infections and can be administered orally and via additional routes. It is available in salt form, for example, the hydrochloride salt, and has the structure:

Celecoxib is a COX-2 inhibitor, taken orally, which is indicated to treat pain or inflammation associated with a variety of conditions. The structure of celecoxib is:

PCT Patent Application Publication WO 2018/235082, incorporated herein by reference, discloses combinations of ciprofloxacin and celecoxib for treatment of a variety of motor neuron diseases, including, but not limited to, amyotrophic lateral sclerosis (ALS).

SUMMARY

Described herein are extended release compositions such as a tablet, that comprise ciprofloxacin or pharmaceutically acceptable salt thereof, and celecoxib. For example, provided herein is a tablet comprising celecoxib and a pharmaceutically acceptable salt of ciprofloxacin, and low viscosity hydroxypropyl methylcellulose having a viscosity of between 2 cP and 150 cP, when measured as a 2% solution in water at 20° C.

Further described herein are processes for manufacture of a tablet comprising: forming granules comprising celecoxib and ciprofloxacin or pharmaceutically acceptable salt of ciprofloxacin; adding a low viscosity hydroxypropyl methylcellulose having a viscosity of less than 150 cP, when measured as a 2% solution in water at 20° C. to the granules, to form a mixture; and compressing the mixture to form a tablet.

Further described herein are methods for treatment amyotrophic lateral sclerosis (ALS) to a patient in need thereof, comprising administering to the patient a composition comprising ciprofloxacin or pharmaceutically acceptable salt thereof, and celecoxib.

The foregoing and other objects, features, and advantages will become more apparent from the following detailed description, which proceeds with reference to the accompanying figures.

DETAILED DESCRIPTION

Terms

Unless otherwise noted, technical terms are used according to conventional usage. Definitions of common terms in molecular biology can be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." The abbreviation, "e.g." is derived from the Latin exempli gratia and is used herein to indicate a non-limiting example. Thus, the abbreviation "e.g." is synonymous with the term "for example."

In case of conflict, the present specification, including explanations of terms, will control. In addition, all the materials, methods, and examples are illustrative and not intended to be limiting.

Extragranular: In processes for formation of tablets, frequently, granules are formed comprising an active ingredient in combination with at least one excipient. A granulation process transforms fine powders into free-flowing, dust-free granules that are easy to compress. The granules can then be mixed by blending with additional excipients or active ingredients. The final blend is then filled into capsules or compressed into tablets. The term "extragranular" refers to the part of the tablet that is not the granule.

Intragranular: The part of the composition that is within the granule, in a tablet composition formed through a granulation process.

Pharmaceutically acceptable salt: A "salt" is a salt of an active compound, such as ciprofloxacin, which has been modified by making acid or base salts of the compounds. It refers to the relatively non-toxic, inorganic and organic acid or base addition salts of compounds of the present invention. These salts can be prepared in situ in the process of preparing the pharmaceutical dosage form, or by separately reacting a purified compound of the invention in its free base form with a suitable organic or inorganic acid, and isolating the salt formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, and mesylate.

Steady State: when the quantity of drug eliminated in the unit of time equals the quantity of the drug that reaches the systemic circulation in the unit of time.

Overview of Several Embodiments

Provided herein are compositions comprising celecoxib and ciprofloxacin or a pharmaceutically acceptable salt of ciprofloxacin.

For example, compositions are provided wherein the ratio of celecoxib to ciprofloxacin or a pharmaceutically salt thereof, based on the weight of celecoxib to the weight of the ciprofloxacin free base is between 1:1 to 1:100, optionally, 1:4, 1:10, 1:25. Exemplary tablets described herein comprise 34 mg of celecoxib per tablet, and 340 mg of ciprofloxacin or a pharmaceutically acceptable salt of ciprofloxacin, in an amount to deliver 340 mg ciprofloxacin (for example 377.41 mg of ciprofloxacin HCl per dosage form, or tablet which corresponds to 340 mg of ciprofloxacin free base) thereby having a celecoxib to ciprofloxacin free base ratio, by weight, of 1:10.

According to some embodiments, compositions comprising celecoxib and ciprofloxacin or a pharmaceutically salt thereof have one, or more than one of the following dissolution characteristics:

1. Dissolution of ciprofloxacin of less than 70%, preferably between 40% and 65% within two hours, when placed in 750 ml of 0.1N HCl, in a Type II apparatus, at 75 revolutions per minute (RPM).
2. Dissolution of ciprofloxacin of less than 80%, preferably between 40% and 65% within two hours, when placed in 750 ml of 0.1N HCl, in a Type II apparatus, at 100 revolutions per minute (RPM) at 37° C.
3. Dissolution of a total of at least 70% ciprofloxacin within 6 hours and/or less than 75% within 4 hours when placed in 750 ml of 0.1N HCl, in a Type II apparatus, at 75 RPM, 37° C. then after two hours, medium is modified to form phosphate buffer at pH of 6.8, comprising 1% SLS.
4. Dissolution of a total of at least 80% ciprofloxacin within 6 hours and/or less than 80% within 4 hours when placed in 750 ml of 0.1N HCl, in a Type II apparatus, at 100 RPM, 37° C. then after two hours, medium is modified to form phosphate buffer at pH of 6.8, comprising 1% SLS.
5. Dissolution of a total of at least 80% celecoxib within 12 hours and/or less than 85% within 8 hours more preferably less than 80% within 8 hours when placed in 750 ml of 0.1N HCl, in a Type II apparatus, at 75 RPM, 37° C. then after two hours, medium is modified to form phosphate buffer at pH of 6.8, comprising 1% SLS.
6. Dissolution of a total of at least 80% celecoxib within 8 hours and/or less than 80% within 6 hours when placed in 750 ml of 0.1N HCl, in a Type II apparatus, at 100 RPM. 37° C., then after two hours, medium is modified to form phosphate buffer at pH of 6.8, comprising 1% SLS.
7. Dissolution of a total of more than 45% of both ciprofloxacin and celecoxib at 3 hours, and less than 90% at 6 hours, when placed in 750 ml of 0.1N HCl, in a Type II apparatus, at 75 RPM, 37° C. then after two hours, medium is modified to form phosphate buffer at pH of 6.8, comprising 1% SLS.
8. Dissolution of between 10% and 30% ciprofloxacin and celecoxib at 1 hour, between 30% and 70% ciprofloxacin and celecoxib at 4 hours, and more than 85% ciprofloxacin and celecoxib at 12 hours, when placed in 900 ml of acetate buffer pH 4.5, in a Type II apparatus, at 75 RPM, 37° C. comprising 1% SLS.

According to some embodiments, compositions comprise low viscosity hydroxypropyl methylcellulose (HPMC). HPMC is a binder and control release agent used in matrix systems of oral pharmaceutical dosage forms such as tablets. HPMC is an excipient that comprises a cellulose backbone having monomers that are substituted methyl groups and hydroxypropyl groups. The amount of substitution can determine properties of the HPMC. One of the properties of HPMC is its viscosity, which is typically measured as a 2% solution in water at 20° C. Preferably, HPMC used in compositions described herein has low viscosity, which is below 150 centipoise (cP) and above 2 cP. Preferably, HPMC used in compositions has a viscosity of between 40 and 60 cP.

Exemplary HPMC types are described below.

| Manufacturer | Trade name/designation | Viscosity (cP) |
|---|---|---|
| Shin Etsu, Japan | Pharmacoat 603 | 3 (2.4-3.6) |
| Shin Etsu, Japan | Pharmacoat 645 | 4.5 (3.6-5.4) |
| Shin Etsu, Japan | Pharmacoat 606 | 6 (4.7-7.2) |
| Shin Etsu, Japan | Pharmacoat 615 | 15 (12.0-18.0) |
| DuPont de Nemours, Inc, Delaware, USA (Dupont) | Methocel E50LV | 50 |
| Dupont | Methocel E15 Premium LV | 15 |
| Dupont | Methocel K100LV | 80-120 |

Pharmacoat 603, 645, 606, and 615 are exemplary HPMC having a viscosity of less than 150 cP, and having Methoxyl: 29% (28.0%-30.0%), Hydroxypropoxyl: 10%. (7.0%-12.0%)

Methocel E50 LV is an exemplary HPMC having a viscosity of less than 150 cP and having Methoxyl: 29% (28.0%-30.0%), Hydroxypropoxyl: 10% (7.0%-12.0%).

Methocel E15 Premium LV is an exemplary HPMC having a viscosity of less than 150 cP, and having Methoxyl: 29% (28.0%-30.0%), Hydroxypropoxyl: 10% (7.0%-12.0%).

Methocel K100 LV is an exemplary HPMC having a viscosity of less than 150 cP, and having Methoxyl: 19.0-24.0%, Hydroxypropoxyl: 7.0-12.0%, Viscosity, 2% in water at 20° C.: 80-120 cP, Moisture, as packaged: 3.0 Max.

Preferably, the amount of HPMC present in the composition is between 3% and 10% percent, by weight of the composition. Optionally, the amount of HPMC present in the composition is 5% by weight of the tablet core.

Preferably, the amount of HPMC present in the composition is between 4% and 15%, relative to the total weight of the active ingredients of the tablet, celecoxib and the ciprofloxacin salt. Preferably, the amount of HPMC by weight present in the composition is between 6 and 8 percent, relative to the combined weight of the active ingredients of the tablet. Preferably, the amount of HPMC is 7% relative to the combined weight of the active ingredients of the dosage form. Preferably, the HPMC is present in the extragranular portion of the tablet, and preferably, the active ingredients are present in the intragranular portion of the tablet.

For example, contemplated herein is a tablet having intragranular components comprising ciprofloxacin and celcocoxib, a filler, a binder and optionally a wetting agent; and an extragranular composition comprising the HPMC, a filler and optionally a flowing agent and/or a lubricant.

The active ingredients celecoxib and ciprofloxacin HCl are different in that celecoxib is a very poorly soluble drug with an estimated solubility in plain water of about 4.3 mg/L at 25° C. (estimated) and ciprofloxacin HCl is a soluble drug with a solubility in water of about 30 grams per liter. The differences in solubility are especially pronounced in acidic media. Without being bound by theory, the compositions described herein may provide optimal therapeutic effect by being delivered through extended release of both ingredients over more than 4 hours. An in vitro test, in which the tablet/dosage form is introduced into 750 ml of 0.1N HCl, in a Type II apparatus for two hours at 100 or 75 RPM, then the medium is modified to form pH 6.8 phosphate buffer having 1% SLS is representative of a human subject, introducing a tablet/dosage form into the stomach, where the tablet remains for approximately two hours, then is passed to the intestine. The tablet slowly releases active ingredients (ciprofloxacin and celecoxib) over the course of more than 2 hours.

Testing of compositions described herein in humans showed that after administration in the fed state, and upon reaching "steady state," the time after administration in which maximal serum concentration of celecoxib ($T_{max}$) was similar to the $T_{max}$ of ciprofloxacin. Without being bound by theory, it is suggested that enhanced synergistic effect of the combination of ciprofloxacin and celecoxib can be obtained when Tmax of both of the active ingredients occurs substantially at the same time or within 80% to 125% of the amount of time after administration with food and water.

Methods of Treatment

Compositions described herein may be used for treatment of ALS in patients in need thereof. A composition may be administered once daily, twice daily, three times daily, or four times daily to a patient in need thereof. The administration may reduce or alleviate a symptom of ALS or prevent progression of ALS upon administration. The composition is preferably administered with food and water.

The following examples are provided to illustrate certain particular features and/or embodiments. These examples should not be construed to limit the disclosure to the particular features or embodiments described.

EXAMPLES

Example 1A: Preparation of Immediate Release (IR) Capsules Comprising Ciprofloxacin HCl and Celecoxib IR capsules were prepared by mixing ciprofloxacin hydrochloride (HCl) in an amount of 377.41 mg per capsule, with celecoxib, in an amount of 34.00 mg per capsule. The mixture was filled in #0 gelatin capsules.

Example 1B: Dissolution of IR Capsules

IR capsules prepared as in Example 1A were tested for dissolution using 750 ml of 0.1N HCl, for one hour followed by addition of 250 ml phosphate buffer to form a pH 6.8 phosphate buffer, with 1% sodium lauryl sulphate.

TABLE 1

| Time (hours) | % Celecoxib | % RSD | % Ciprofloxacin | % RSD |
|---|---|---|---|---|
| 0.5 | 0 | 0 | 80 | 1.4 |
| 1 | 0 | 0 | 88 | 2.0 |
| 2 | 73 | 8.1 | 85 | 2.4 |
| 3 | 82 | 10.6 | 86 | 3.0 |
| 4 | 86 | 11.8 | 87 | 4.7 |
| 6 | 90 | 8.9 | 87 | 3.4 |
| 8 | 92 | 8.7 | 87 | 3.9 |
| 10 | 94 | 7.5 | 87 | 3.3 |
| 12 | 96 | 6.3 | 88 | 3.7 |

Conditions of the dissolution test in this example were designed to simulate administration of a capsule prepared as in example 1A to a human patient, in which the capsule would remain in the stomach acidic condition for about 1 hour, then pass into the intestine, where the pH is closer to 6.8. As can be seen from Table 1, Ciprofloxacin almost fully dissolved while Celecoxib was not released after 1 hr in 0.1N HCl. Dissolution of both celecoxib and ciprofloxacin was rapid, after addition of 250 ml phosphate buffer to form a pH 6.8 phosphate buffer, with 1% sodium lauryl sulphate and within a few hours of administration to a human, all of the ciprofloxacin would be released. A profile providing a longer release time of ciprofloxacin was desired.

Example 2A: Preparation of Extended Release (ER) Tablets Comprising Ciprofloxacin HCl and Celecoxib A tablet matrix composition (designated batch 08) was developed to take into account the different solubilities of the two actives, ciprofloxacin and celecoxib, and to provide a longer release time of ciprofloxacin, which would begin in the acidic conditions of the stomach, and continue while the dosage form was passed through the intestine.

The following active ingredients and excipients, from the specified suppliers, were used in the tablet compositions:
Ciprofloxacin Hydrochloride, USP; Neuland India
Celecoxib, USP; HiKAL, India
Microcrystalline cellulose, USP, NF; FMC International, Cork, Ireland.
Povidone K-30 USP, NF; BASF, Germany.
Sodium lauryl sulphate, USP, NF; BASF, Germany.
Hydroxy propyl methyl cellulose, USP, EP Dow
Colloidal Silicon Dioxide USP, NF Evonik
Magnesium Stearate, Ph. Eur.; Peter Greven, Netherlands
The amounts used in the tablet compositions appear in table 2.

TABLE 2

| Ingredient | Brand Name | Function | Amount in mg | Percent relative to active |
|---|---|---|---|---|
| Ciprofloxacin HCl | | Active | 377.41 | |
| Celecoxib | | Active | 34 | |
| Microcrystalline cellulose | Avicel PH102 | Filler | 38.59 | 9.4 |
| Povidone K-30 | Kollidon 30 | Binder | 25 | 6.1 |
| Sodium lauryl sulphate | Kolliphor SLS fine | Wetting Agent | 3.4 | 0.8 |
| Extragranular Materials | | | | |
| HPMC | Methocel E50LV | Control Release/binder Polymer | 28.5 | 6.9 |
| Microcrystalline cellulose | Avicel PH102 | Filler | 51.7 | 12.6 |
| Colloidal Silicon Dioxide | Aerosil 200 | Flowing Agent | 5.7 | 1.4 |
| Magnesium Stearate | | Lubricant | 5.7 | 1.4 |
| Core Tablet Weight | | | 570 | |

Tablets were prepared using the following general procedure:

Sifting: Ciprofloxacin hydrochloride was sifted through a #16 mesh screen, and Celecoxib was sifted through a #16 mesh screen and microcrystalline cellulose/lactose sifted through a #40 mesh screen manually.

A binder solution was prepared by weighting a quantity of sodium lauryl sulphate and Povidone, PVP K-30 which were then added to purified water while stirring, which was continued until a clear solution was obtained.

Dry Mix: The sifted material was loaded in rapid mixer granulator (10 L) and dry mixed for 10 minutes using a slow impeller speed and with the chopper off.

Granulation: Binder solution were added to the dry mix and the wet mass was passed through #10 mesh screen manually.

Drying: Wet granules were dried in a Retsch drier.

Sifting and Milling (Dried Granules): Dried granules were sifted through a #20 mesh screen and sifted granules were collected in a polybag.

Blending and Lubrication: Hydroxy propyl methyl cellulose (METHOCEL E 50 PRE LV), Microcrystalline cellulose (Avicel PH102), and Colloidal Silicon Dioxide (Aerosil 200) were sifted through a #40 mesh screen. Dried granules of the intragranular portion and sifted material of the extragranular portion were then blended (Conta Blender 10L) together for 15 minutes at 15 RPM.

Magnesium stearate was sifted through a #60 mesh screen and added to above blend and lubrication was performed for 5 minutes at 15 RPM. The final blend was compressed.

Example 2B: Dissolution of ER Tablets of Batch 08

A dissolution test of Batch 08 was performed in 750 ml in 0.1N HCl for 2 hours followed by transferring the dosage form to pH 6.8 Phosphate Buffer with 1% SLS, 900 mL, Type II, at 100 RPM. The percentage of drug release at various time points is detailed in Table 3 below.

TABLE 3

| Time (Hr) | % Celecoxib release | % Ciprofloxacin release |
|---|---|---|
| 0 | 0 | 0 |
| 0.5 | 2 | 18 |
| 1 | 5 | 34 |
| 2 | 8 | 59 |
| 3 | 13 | 70 |
| 4 | 16 | 76 |
| 6 | 26 | 85 |
| 8 | 36 | 92 |
| 10 | 46 | 97 |
| 12 | 50 | 100 |

As can be noticed in the above table, only 50% of the Celecoxib drug substance was released after total 12 hours, 2 hours in 0.1N HCl followed by 10 hours in the buffer phosphate medium pH 6. 8+1% SLS.

Example 3A: Preparation of Additional Extended Release (ER) Tablets Comprising Ciprofloxacin HCl and Celecoxib This example uses more soluble filler, such as lactose, in place of the extragranular filler in the Batch 08 composition, to attempt to improve the dissolution of the celecoxib. In addition to adding soluble fillers (lactose), HPMC (METHOCEL E50 LV) polymer which controls and delays the drug release from matrix and has binder properties, was eliminated.

The general manufacturing procedures employed in Example 2A were used, with the excipients described in Table 4 below, to form Batch 36:

TABLE 4

| Ingredient | Brand Name | Function | Amount in mg | Percent relative to active |
|---|---|---|---|---|
| Ciprofloxacin HCl | | Active | 377.41 | |
| Celecoxib | | Active | 34 | |
| Microcrystalline cellulose | Avicel PH102 | Filler | 38.59 | 9.4 |
| Povidone K-30 | Kollidon 30 | Binder | 25 | 6.1 |
| Sodium lauryl sulphate | Kolliphor SLS fine | Wetting Agent | 3.4 | 0.8 |
| Extragranular Materials | | | | |
| Lactose anhydrous | Super Tab 21 AN | Filler | 51.7 | 12.6 |

TABLE 4-continued

| Ingredient | Brand Name | Function | Amount in mg | Percent relative to active |
|---|---|---|---|---|
| Colloidal Silicon Dioxide | Aerosil 200 | Flowing Agent | 5.7 | 1.4 |
| Magnesium Stearate | | Lubricant | 5.7 | 1.4 |
| Core Tablet Weight | | | 541.5 | |

In addition, batch 37 was prepared, in which was lactose was used as the extragranular filler, and lactose monohydrate was used in place of microcrystalline cellulose as the filler in the granulate. The general manufacturing procedures employed in Example 2A were used, with the excipients described in Table 5 below, to form Batch 37:

TABLE 5

| Ingredient | Brand Name | Function | Amount in mg | Percent relative to active |
|---|---|---|---|---|
| Ciprofloxacin HCl | | Active | 377.41 | |
| Celecoxib | | Active | 34 | |
| Lactose monohydrate | Pharmatose 200M | Filler | 38.59 | 9.4 |
| Povidone K-30 | Kollidon 30 | Binder | 25 | 6.1 |
| Sodium lauryl sulphate | Kolliphor SLS fine | Wetting Agent | 3.4 | 0.8 |
| Extragranular Materials | | | | |
| Lactose anhydrous | Super Tab 21 AN | Filler | 51.7 | 12.6 |
| Colloidal Silicon Dioxide | Aerosil 200 | Flowing Agent | 5.7 | 1.4 |
| Magnesium Stearate | | Lubricant | 5.7 | 1.4 |
| Core Tablet Weight | | | 541.5 | |

In addition, batch 38 was prepared, in which lactose was used as the extragranular filler, and a portion of the microcrystalline cellulose in the granulate of batch 08 was substituted with lactose monohydrate. The general manufacturing procedures employed in Example 2A were used, with the excipients described in Table 6 below, to form Batch 38:

TABLE 6

| Ingredient | Brand Name | Function | Amount in mg | Percent relative to active |
|---|---|---|---|---|
| Ciprofloxacin HCl | | Active | 377.41 | |
| Celecoxib | | Active | 34 | |
| Microcrystalline cellulose | Avicel PH102 | Filler | 19 | 4.6 |
| Lactose monohydrate | Pharmatose 200M | Filler | 19.59 | 4.8 |
| Povidone K-30 | Kollidon 30 | Binder | 25 | 6.1 |
| Sodium lauryl sulphate | Kolliphor SLS fine | Wetting Agent | 3.4 | 0.8 |

TABLE 6-continued

| Ingredient | Brand Name | Function | Amount in mg | Percent relative to active |
|---|---|---|---|---|
| Extragranular Materials | | | | |
| Lactose anhydrous | Super Tab 21 AN | Filler | 51.7 | 12.6 |
| Colloidal Silicon Dioxide | Aerosil 200 | Flowing Agent | 5.7 | 1.4 |
| Magnesium Stearate | | Lubricant | 5.7 | 1.4 |
| Core Tablet Weight | | | 541.5 | |

Example 3B: Dissolution of ER Tablets of Batch 08 versus Batch 37

A dissolution test was performed comparing dissolution of tablets prepared from Batch 08 and from Batch 37, in 0.1N HCl for 2 hours followed by transferring the dosage form to pH 6.8 Phosphate Buffer with 1% SLS, 900 mL, Type II, at 100 RPM. The percentage of drug release at various time points is detailed in Table 7 below.

TABLE 7

| | Batch 08 | | Batch 37 | |
|---|---|---|---|---|
| Time (Hr) | % Celecoxib release | % Ciprofloxacin release | % Celecoxib release | % Ciprofloxacin release |
| 0 | 0 | 0 | 0 | 0 |
| 0.5 | 2 | 18 | 0 | 13 |
| 1 | 5 | 34 | 0 | 19 |
| 2 | 8 | 59 | 1 | 27 |
| 3 | 13 | 70 | 17 | 37 |
| 4 | 16 | 76 | 27 | 47 |
| 6 | 26 | 85 | 44 | 64 |
| 8 | 36 | 92 | 59 | 78 |
| 10 | 46 | 97 | 74 | 88 |
| 12 | 50 | 100 | 86 | 95 |
| 16 | n/a | n/a | 94 | 99 |

When comparing tablets of Batch 08 to those of Batch 37, it is evident that there is increased dissolution of celecoxib at 12 hours in Batch 37 (86%) relative to Batch 08. However, the ciprofloxacin did not sufficiently dissolve in the acidic medium in two hours, as evident from the 27% dissolution of Batch 37 relative to the over 50% (59%) of Batch 08. Despite that a more soluble extragranular and intragranular filler was used in Batch 37, the solubility of ciprofloxacin was negatively impacted.

Example 3C: Dissolution of ER Tablets of Batch 08 versus Batches 36, 37 and 38

A dissolution test was performed comparing dissolution of tablets prepared from Batch 08 and from Batch 37, in 0.1N HCl for 2 hours Type II, at 100 RPM. The percentage of drug release at various time points is detailed in Table 8 below. Dissolution was performed simultaneously on 3 tablets of each batch in a 12-unit dissolution apparatus.

TABLE 8

| | Batch No. | | | | | | | |
|---|---|---|---|---|---|---|---|---|
| | 08 | | 36 | | 37 | | 38 | |
| Time (Hr) | % Celecoxib release | % Ciprofloxacin release | % Celecoxib release | % Ciprofloxacin release | % Celecoxib release | % Ciprofloxacin release | % Celecoxib release | % Ciprofloxacin release |
| 0 | 0 | 0 | 0 | 0 | 0 | 0 | 0 | 0 |
| 0.5 | 0 | 21 | 0 | 13 | 0 | 13 | 0 | 12 |
| 1 | 2 | 38 | 0 | 19 | 0 | 18 | 0 | 18 |
| 2 | 4 | 61 | 0 | 28 | 0 | 28 | 0 | 26 |

As evident from Table 8, dissolution of Batches 36, 37 and 38 in 0.1N HCl showed insufficient dissolution of less than 50% (even less than 30%) ciprofloxacin from the tablet. Surprisingly, ciprofloxacin was released more rapidly from tablets of Batch 08, even though they contained HPMC polymer and the non-soluble filler, microcrystalline cellulose. Without being bound by theory this might be due to the faster water imbibing power of HPMC compared to Lactose which impacts the release rate of ciprofloxacin. HPMC imbibes more fluid into the matrix allowing gelling. During this gelling period, in presence of dissolution fluid, Ciprofloxacin starts going into solution in faster rate as its solubility is higher than celecoxib in 0.1N HCl. But as the solubility of Celecoxib is very low in 0.1N HCl, its drug release is minimally affected due to this phenomenon, and more affected by the presence of the soluble lactose filler that cause to faster drug release, upon transfer of the dosage form to phosphate buffer after two hours.

Example 4A: Preparation of Additional Extended Release (ER) Tablets Comprising Ciprofloxacin HCl and Celecoxib Additional tablet compositions were prepared in the method similar to Batch 08. Batch 39A was prepared using excipients described in Table 9 below.

TABLE 9

| Ingredient | Brand Name | Function | Amount in mg | Percent relative to active |
|---|---|---|---|---|
| Ciprofloxacin HCl | | Active | 377.41 | |
| Celecoxib | | Active | 34 | |
| Lactose monohydrate | Pharmatose 200M | Filler | 38.59 | 9.4 |
| Povidone K-30 | Kollidon 30 | Binder | 25 | 6.1 |
| Sodium lauryl sulphate | Kolliphor SLS fine | Wetting Agent | 3.4 | 0.8 |
| Extragranular Materials | | | | |
| HPMC | Methocel E15 LV | Binder and Control Release Polymer | 28.5 | 6.9 |
| Lactose anhydrous | Super Tab 21 AN | Filler | 51.7 | 12.6 |
| Colloidal Silicon Dioxide | Aerosil 200 | Flowing Agent | 5.7 | 1.4 |
| Magnesium Stearate | | Lubricant | 5.7 | 1.4 |
| Core Tablet Weight | | | 570 | |

The core tablet was coated with Opadry Blue, in an amount of 17.1 mg per tablet. In this composition, lactose was used as an intragranular filler and as an extragranular filler as opposed to microcrystalline cellulose in Batch 08. A different HPMC polymer was also used—Methocel E15 LV.

Batch 39B was prepared using excipients described in Table 10 below.

TABLE 10

| Ingredient | Brand Name | Function | Amount in mg | Percent relative to active |
|---|---|---|---|---|
| Ciprofloxacin HCl | | Active | 377.41 | |
| Celecoxib | | Active | 34 | |
| Lactose monohydrate | Pharmatose 200M | Filler | 38.59 | 9.4 |
| Povidone K-30 | Kollidon 30 | Binder | 25 | 6.1 |
| Sodium lauryl sulphate | Kolliphor SLS fine | Wetting Agent | 3.4 | 0.8 |
| Extragranular Materials | | | | |
| HPMC | Pharmacoat 606 | Control Release Polymer | 28.5 | 6.9 |
| Lactose anhydrous | Super Tab 21 AN | Filler | 51.7 | 12.6 |
| Colloidal Silicon Dioxide | Aerosil 200 | Flowing Agent | 5.7 | 1.4 |
| Magnesium Stearate | | Lubricant | 5.7 | 1.4 |
| Core Tablet Weight | | | 570 | |

The core tablet was coated with Opadry Blue, in an amount of 17.1 mg per tablet. Tablets made according to Batch 39B were similar to those of Batch 39A, with the difference that a different type of HPMC was used.

Batch 40A was prepared using excipients described in Table 11 below.

TABLE 11

| Ingredient | Brand Name | Function | Amount in mg | Percent relative to active |
|---|---|---|---|---|
| Ciprofloxacin HCl | | Active | 377.41 | |
| Celecoxib | | Active | 34 | |
| Lactose monohydrate | Pharmatose 200M | Filler | 38.59 | 9.4 |
| Povidone K-30 | Kollidon 30 | Binder | 25 | 6.1 |
| Sodium lauryl sulphate | Kolliphor SLS fine | Wetting Agent | 3.4 | 0.8 |
| Extragranular Materials | | | | |
| HPMC | Methocel E15 LV | Binder & Control Release Polymer | 28.5 | 6.9 |

TABLE 11-continued

| Ingredient | Brand Name | Function | Amount in mg | Percent relative to active |
|---|---|---|---|---|
| Microcrystalline cellulose | Avicel PH102 | Filler | 51.7 | 12.6 |
| Colloidal Silicon Dioxide | Aerosil 200 | Flowing Agent | 5.7 | 1.4 |
| Magnesium Stearate | | Lubricant | 5.7 | 1.4 |
| Core Tablet Weight | | | 570 | |

The core tablet was coated with Opadry Blue, in an amount of 17.1 mg per tablet. This composition was similar Batch 08, but a different HPMC polymer was used, Methocel E15 LV.

Batch 40B was prepared using excipients described in Table 12 below.

TABLE 12

| Ingredient | Brand Name | Function | Amount in mg | Percent relative to active |
|---|---|---|---|---|
| Ciprofloxacin HCl | | Active | 377.41 | |
| Celecoxib | | Active | 34 | |
| Lactose monohydrate | Pharmatose 200M | Filler | 38.59 | 9.4 |
| Povidone K-30 | Kollidon 30 | Binder | 25 | 6.1 |
| Sodium lauryl sulphate | Kolliphor SLS fine | Wetting Agent | 3.4 | 0.8 |
| Extragranular Materials | | | | |
| HPMC | Pharmacoat 606 | Binder &Control Release Polymer | 28.5 | 6.9 |
| Microcrystalline cellulose | Avicel PH102 | Filler | 51.7 | 12.6 |
| Colloidal Silicon Dioxide | Aerosil 200 | Flowing Agent | 5.7 | 1.4 |
| Magnesium Stearate | | Lubricant | 5.7 | 1.4 |
| Core Tablet Weight | | | 570 | |

The core tablet was coated with Opadry Blue, in an amount of 17.1 mg per tablet. This composition was similar Batch 08, but a different HPMC polymer was used, Methocel E15 LV.

Example 4B: Dissolution of ER Tablets

A dissolution test was performed comparing dissolution of tablets prepared from Batches 39A, 39B, 40A and 40B, in 0.1N HCl for 2 hours, Type II, at 100 RPM. The percentage of drug release at various time points, in minutes, is detailed in Table 13 below.

TABLE 13

| % Active release | Batch | | | | | | | |
|---|---|---|---|---|---|---|---|---|
| | 39A | | 39B | | 40A | | 40B | |
| min | Celecoxib | Ciprofloxacin | Celecoxib | Ciprofloxacin | Celecoxib | Ciprofloxacin | Celecoxib | Ciprofloxacin |
| 30 | 1 | 25 | 1 | 22 | 1 | 15 | 1 | 14 |
| 60 | 5 | 48 | 5 | 43 | 3 | 31 | 4 | 27 |
| 120 | 7 | 79 | 7 | 73 | 6 | 55 | 6 | 50 |

The presence of various types of low viscosity HPMC, as in batches 39A, 39B, 40A and 40B, were effective in increasing dissolution of ciprofloxacin to acceptable levels of 50% and above in 0.1N HCl for 2 hours. When comparing dissolution of batches 39A and 39B to 40A and 40B, it appears that use of lactose as a diluent as opposed to microcrystalline cellulose provides faster ciprofloxacin dissolution levels.

Example 5: Alternate Dissolution Method

The method described in Example 2B showed only limited (50%) celecoxib release after 12 hours. The rapid release of ciprofloxacin in the acidic medium may result in partial tablet disintegration, and therefore the tablet may not be completely transferred from the acidic medium, therefore an alternate method was also used.

An alternate method was performed in which tablets were put in 750 ml of 0.1N HCl for 2 hours, followed by addition of 250 ml to form a pH 6.8 phosphate buffer with 1% SLS. This process is performed while stirring at 100 RPM. This method prevented handling of the tablet and transfer between media.

The results of this dissolution test, performed on tablets from batch 08 are shown in table 14 below.

TABLE 14

| Time (Hr) | % Celecoxib release | % Ciprofloxacin release |
|---|---|---|
| 0 | 0 | 0 |
| 0.5 | 0 | 20 |
| 1 | 0 | 36 |
| 2 | 2 | 60 |
| 3 | 65 | 71 |
| 4 | 70 | 76 |
| 6 | 78 | 85 |
| 8 | 85 | 92 |
| 10 | 90 | 97 |
| 12 | 95 | 100 |

An alternate method was performed in which tablets were put in 750 ml of 0.1N HCl for 2 hours, followed by addition of 250 ml to form a pH 6.8 phosphate buffer with 1% SLS. This process is performed while stirring at 75 RPM The results of this dissolution test, performed on tablets from batch 08 are shown in table 15 below.

TABLE 15

| | Batch 08 | | Batch 39B | |
|---|---|---|---|---|
| Hr | % Celecoxib | % Ciprofloxacin | % Celecoxib | % Ciprofloxacin |
| 0.5 | 0 | 17 | 0 | 17 |
| 1 | 1 | 30 | 1 | 33 |

TABLE 15-continued

| | Batch 08 | | Batch 39B | |
|---|---|---|---|---|
| Hr | % Celecoxib | % Ciprofloxacin | % Celecoxib | % Ciprofloxacin |
| 2 | 2 | 51 | 3 | 60 |
| 3 | 54 | 60 | 61 | 67 |
| 4 | 56 | 63 | 65 | 71 |
| 6 | 64 | 72 | 73 | 79 |
| 8 | 71 | 79 | 79 | 85 |
| 10 | 78 | 87 | 85 | 90 |
| 12 | 84 | 93 | 91 | 95 |
| 14 | 89 | 97 | 95 | 99 |
| 16 | 94 | 100 | 99 | 102 |

As evident from Tables 14 and 15 when using this method, as compared to the method shown in Table 3, nearly complete dissolution at levels above 80% of celecoxib in Batches 08, 39B is obtained within 8-12 hours at 100 RPM or 12-16 hours at 75 RPM. Compositions from batches 39A, 40A, and 40B will behave similarly when subject to this method. The dissolution was not significantly different when comparing compositions with soluble fillers and non-soluble fillers.

In summary, compositions comprising low viscosity HPMC were effective in dissolution of ciprofloxacin to acceptable levels of less than 70%, preferably between 40% and 65% in 0.1N HCl for 2 hours, while maintaining dissolution at levels above 80% over 10 hours in this method at 75 RPM and over 6 hours at 100 RPM.

Example 6A: Additional Tablet Compositions

Additional tablet compositions were prepared in the method similar to Batch 08. Batch 2D was prepared using excipients described in Table 16 below. Batch 2D represents a batch in which the amount of HPMC was 20% of the tablet weight.

TABLE 16

| Ingredient | Brand Name | Function | Amount in mg | Percent relative to active |
|---|---|---|---|---|
| Ciprofloxacin HCl | | Active | 377.41 | |
| Celecoxib | | Active | 34 | |
| Microcrystalline cellulose | Avicel PH102 | Filler | 38.59 | 9.4 |
| Povidone K-30 | Kollidon 30 | Binder | 18.2 | 4.4 |
| Sodium lauryl sulphate | Kolliphor SLS fine | Wetting Agent | 3.4 | 0.8 |
| Extragranular Materials | | | | |
| HPMC | Methocel K100 LV | Binder and Control Release Polymer | 140 | 34 |
| Microcrystalline cellulose | Avicel PH102 | Filler | 74.4 | 18.1 |
| Colloidal Silicon Dioxide | Aerosil 200 | Flowing Agent | 7 | 1.7 |
| Magnesium Stearate | | Lubricant | 7 | 1.7 |
| Core Tablet Weight | | | 700 | |

Batch 05E was prepared using excipients described in Table 17 below and represents a batch in which the amount of HPMC was 10% of the tablet weight.

TABLE 17

| Ingredient | Brand Name | Function | Amount in mg | Percent relative to active |
|---|---|---|---|---|
| Ciprofloxacin HCl | | Active | 377.41 | |
| Celecoxib | | Active | 34 | |
| Microcrystalline cellulose | Avicel PH102 | Filler | 38.59 | 9.4 |
| Povidone K-30 | Kollidon 30 | Binder | 25.0 | 6.1 |
| Sodium lauryl sulphate | Kolliphor SLS fine | Wetting Agent | 3.4 | 0.8 |
| Extragranular Materials | | | | |
| HPMC | Methocel E50LV | Binder and Control Release Polymer | 60.0 | 14.6 |
| Microcrystalline cellulose | Avicel PH102 | Filler | 49.6 | 12.1 |
| Colloidal Silicon Dioxide | Aerosil 200 | Flowing Agent | 6.0 | 1.5 |
| Magnesium Stearate | | Lubricant | 6.0 | 1.5 |
| Core Tablet Weight | | | 600 | |

Additional tablet compositions were prepared in the method similar to Batch 08. Batch 05B was prepared using excipients described in Table 18 below. Batch 05B represents a batch in which the type of HPMC was Methocel K100 LV in an amount of 5% of the tablet weight.

TABLE 18

| Ingredient | Brand Name | Function | Amount in mg | Percent relative to active |
|---|---|---|---|---|
| Ciprofloxacin HCl | | Active | 377.41 | |
| Celecoxib | | Active | 34 | |
| Microcrystalline cellulose | Avicel PH102 | Filler | 38.59 | 9.4 |
| Povidone K-30 | Kollidon 30 | Binder | 18.2 | 4.4 |
| Sodium lauryl sulphate | Kolliphor SLS fine | Wetting Agent | 3.4 | 0.8 |
| Extragranular Materials | | | | |
| HPMC | Methocel K100 LV | Binder and Control Release Polymer | 30 | 7.3 |
| Microcrystalline cellulose | Avicel PH102 | Filler | 50.20 | 12.2 |
| Colloidal Silicon Dioxide | Aerosil 200 | Flowing Agent | 5.70 | 1.4 |
| Magnesium Stearate | | Lubricant | 5.70 | 1.4 |
| Core Tablet Weight | | | 570 | |

Batch 05F represents a batch in which the amount of HPMC Methocel E50LV was 5% of the tablet weight as batch 08.

TABLE 18

| Ingredient | Brand Name | Function | Amount in mg | Percent relative to active |
|---|---|---|---|---|
| Ciprofloxacin HCl | | Active | 377.41 | |
| Celecoxib | | Active | 34 | |
| Microcrystalline cellulose | Avicel PH102 | Filler | 38.59 | 9.4 |

TABLE 18-continued

| Ingredient | Brand Name | Function | Amount in mg | Percent relative to active |
|---|---|---|---|---|
| Povidone K-30 | Kollidon 30 | Binder | 18.2 | 4.4 |
| Sodium lauryl sulphate | Kolliphor SLS fine | Wetting Agent | 3.4 | 0.8 |
| Extragranular Materials | | | | |
| HPMC | Methocel E 50 LV | Binder and Control Release Polymer | 28.50 | 7.3 |
| Microcrystalline cellulose | Avicel PH102 | Filler | 51.70 | 12.2 |
| Colloidal Silicon Dioxide | Aerosil 200 | Flowing Agent | 5.70 | 1.4 |
| Magnesium Stearate | | Lubricant | 5.70 | 1.4 |
| Core Tablet Weight | | | 570 | |

Example 6B: Dissolution of ER Tablets of Batch 2D versus Batch 05E, and 05B

A dissolution test was performed comparing dissolution of tablets prepared from Batches 2D, 05E, and 05B in a medium having pH of 12, at 75 RPM. The percentage of drug release at various time points, in minutes, is detailed in Table 19 below.

TABLE 19

| | Batch | | | | | | | |
|---|---|---|---|---|---|---|---|---|
| | 2D | | 05E | | 05B | | 05F | |
| Active | Celecoxib | Ciprofloxacin | Celecoxib | Ciprofloxacin | Celecoxib | Ciprofloxacin | Celecoxib | Ciprofloxacin |
| 30 | 6 | 9 | 12 | 13 | 18 | 21 | 16 | 19 |
| 60 | 13 | 17 | 26 | 28 | 35 | 38 | 34 | 37 |
| 120 | 30 | 35 | 51 | 53 | 64 | 67 | 65 | 68 |
| 180 | 46 | 51 | 71 | 73 | 81 | 83 | 84 | 87 |
| 240 | No Data | No Data | 87 | 89 | 92 | 93 | 97 | 99 |

This medium having pH of 12 was used in light of the pharmacopeial testing of immediate release tablets of celecoxib. As seen from Table 19, compositions from Batch 05B, and 05F as batch 08 gave similar dissolution profile release of each active ingredient in pH 12 medium. Composition from batch 05E, having 10% by weight HPMC Methocel E 50 LV and 05B, having 5% by weight HPMC Methocel K100LV, did show a promising release profile, releasing more than 40%, even 50% of actives within two hours. Composition of Batch 2D, in which the amount of HPMC Methocel K 100 LV was 20% of the tablet weight gave slower dissolution profile release of both active ingredient in pH 12 medium.

Example 6C

Additional tablet compositions were prepared in the method similar to Batch 08. Batch 19C was prepared using excipients described in Table 20 below. Batch 19C represents a batch in which the amount of HPMC was 3% of the tablet weight.

TABLE 20

| Ingredient | Brand Name | Function | Amount in mg | Percent relative to active |
|---|---|---|---|---|
| Ciprofloxacin HCl | | Active | 377.41 | |
| Celecoxib | | Active | 34 | |
| Microcrystalline cellulose | Avicel PH102 | Filler | 38.59 | 9.4 |
| Povidone K-30 | Kollidon 30 | Binder | 25.0 | 6.1 |
| Sodium lauryl sulphate | Kolliphor SLS fine | Wetting Agent | 3.4 | 0.8 |
| Extragranular Materials | | | | |
| HPMC | Methocel E50 LV | Binder and Control Release Polymer | 17.10 | 4.2 |
| Microcrystalline cellulose | Avicel PH102 | Filler | 63.10 | 15.3 |
| Colloidal Silicon Dioxide | Aerosil 200 | Flowing Agent | 5.70 | 1.4 |
| Magnesium Stearate | | Lubricant | 5.70 | 1.4 |
| Core Tablet Weight | | | 570 | |

Example 6D: Dissolution of ER Tablets of Batch 19C

A dissolution test was performed to determine dissolution of tablets prepared from Batch 19C in a medium of 900 ml 0.1N HCl for two hours, at 100 RPM. The percentage of drug release at various time points, in minutes, is detailed in Table 21 below.

TABLE 21

| | Batch 19C | |
|---|---|---|
| Active | % Celecoxib Release | % Ciprofloxacin Release |
| 30 | 1 | 22 |
| 60 | 4 | 43 |
| 120 | 7 | 69 |

Despite a relatively small amount of HPMC used in Batch 19C of 3% of tablet core weight, 4.1% relative to active, after 2 hours in 0.1N HCl media the dissolution of ciprofloxacin was above 50%.

Example 6E: Dissolution of ER Tablets in Conditions Comparable to "fed" Conditions Extended Release (ER) Tablets were prepared as in example 2A, with the exception that each tablet was coated with a film coating using a hypromellose-based film, Opadry® Blue, (Opadry blue 13B 5050008 IH; Colorcon, India) in an amount of 17.10 mg/tablet. These tablets were designated ERPC.

A dissolution test was performed comparing dissolution of tablets prepared from Batches 08 and ERPC in a medium having pH of 4.5 using acetate buffer 1% SLS, 900 ml, at 75 RPM, USP II, with a sinker. The percentage of drug release at various time points, in minutes, is detailed in Table 22 below. This media was chosen to replicate administration to subjects under fed conditions.

TABLE 22

| Time (Hours) | % Drug release of Celecoxib | | | | % Drug release of Ciprofloxacin | | | |
|---|---|---|---|---|---|---|---|---|
| | 08 | | ERPC | | 08 | | ERPC | |
| | % Release | % RSD | % Release | % RSD | % Release | % RSD | % Release | % RSD |
| 1 | 9 | 44.0 | 12 | 39.5 | 17 | 21.3 | 20 | 21.9 |
| 2 | 20 | 42.7 | 24 | 39.5 | 32 | 22.6 | 36 | 23.2 |
| 4 | 43 | 29.0 | 46 | 32.0 | 57 | 18.0 | 61 | 19.6 |
| 6 | 59 | 17.8 | 66 | 24.7 | 75 | 10.5 | 80 | 14.1 |
| 8 | 77 | 12.7 | 84 | 13.8 | 90 | 7.5 | 94 | 7.5 |
| 10 | 91 | 7.7 | 94 | 4.8 | 98 | 3.3 | 100 | 1.9 |
| 12 | 99 | 1.4 | 98 | 0.8 | 102 | 1.2 | 102 | 0.8 |
| 16 | 100 | 0.8 | 98 | 0.7 | 103 | 0.8 | 102 | 0.6 |
| 20 | 100 | 0.6 | 99 | 0.4 | 103 | 0.3 | 102 | 0.8 |
| 24 | 101 | 0.4 | 98 | 0.7 | 103 | 0.5 | 102 | 0.8 |

At one hour into the dissolution test, mean release of both celecoxib and ciprofloxacin was between 10% and 30%. At four hours into the dissolution test, mean release of both celecoxib and ciprofloxacin was between 30% and 70%. At 12 hours mean dissolution of both celecoxib and ciprofloxacin was more than 85%. These results indicate that under fed conditions, these compositions could provide similar profiles for dissolution of both celecoxib and ciprofloxacin in humans.

Example 7: Testing of Tablets Comprising Celecoxib and Ciprofloxacin HCl in Humans Extended Release (ER) Tablets were prepared as in example 2A, with the exception that each tablet was coated with a film coating using a hypromellose-based film, Opadry® Blue, (Opadry blue 13B 5050008 IH; Colorcon, India) in an amount of 17.10 mg/tablet. These tablets were used in the human trials, and were designated ERPC.

An open-label, randomized, multiple-dose, two-treatment, crossover study was performed to evaluate the comparative bioavailability of ERPC, a fixed dose combination tablet composed of celecoxib and ciprofloxacin HCl, relative to reference products. The reference products were CIPRO® tablets (ciprofloxacin HCl, Bayer) co-administered with CELBREX® capsules (celecoxib, Pfizer), when administered every 12 hours for 6.5 days, for a total of 13 administrations in healthy adult males and females, under fed conditions.

Pharmacokinetic Analysis

Concentration data was checked to identify pre-dose concentrations greater than 5% of $C_{max}$ for morning dose of Day 1. None of the subjects were identified with pre-dose concentration greater than 5% of $C_{max}$ for morning dose of Day 1.

Summary of Pharmacokinetic Parameters

Employing the estimated concentration vs. time profiles of ciprofloxacin and celecoxib, pharmacokinetic parameters were computed for ciprofloxacin and celecoxib, using non-compartmental model of Phoenix® WinNonlin® Version 8.3 (Certara L.P.).

The Test Treatment consisted of a morning dose of 2 tablets of ERPC, 680 mg oral dose of ciprofloxacin and 68 mg oral dose of celecoxib in the form of 2 ERPC Tablets and an evening dose of 2 tablets of ERPC, comprising 680 mg oral dose of ciprofloxacin and 68 mg oral dose of celecoxib. The reference treatment consisted of a morning dose of 750 mg oral dose of ciprofloxacin of Cipro® tablets (1×500 mg tablet and 1×250 mg tablet) co-administered with 200 mg oral dose of celecoxib of Celebrex® capsules (1×200 mg capsule), and an evening dose of 750 mg oral dose of ciprofloxacin of Cipro® tablets (1×500 mg tablet and 1×250 mg tablet) co-administered with 200 mg oral dose of celecoxib of Celebrex® capsules (1×200 mg capsule). For both study treatments, the morning dose on Days 1-7 was administered to subjects at 30 minutes following the start of a normocaloric meal that was preceded by a fast of at least 10 hours. The evening dose on Days 1-6 was administered to subjects at 30 minutes following the start of a normo-caloric meal that was preceded by a fast of at least 2 hours. Pharmacokinetic parameters (mean) of ciprofloxacin and celecoxib were computed and are depicted in below in Table 23 for ciprofloxacin values and Table 24 for celecoxib values:

TABLE 23

| | | Mean ± SD (untransformed data) | |
|---|---|---|---|
| Day | Parameters (Units) | Test Treatment (N = 19) | Reference Product (N = 19) |
| Day 1 | $T_{max, D1}$ (h)* | 5.00 (3.00-10.00) | 3.00 (1.50-5.05) |
| | $C_{max, D1}$ (ng/mL) | 888.671 ± 274.2466 | 1072.119 ± 606.2951 |
| | $AUC_{0-12, D1}$ (ng · h/mL) | 4268.911 ± 1337.1035 | 5543.366 ± 2528.2761 |
| | $\lambda_{Z, D1}$ (h$^{-1}$) | 0.156 ± 0.0368 | 0.153 ± 0.0338 |
| | $t_{1/2, D1}$ (h) | 4.796 ± 1.7320 | 4.807 ± 1.3240 |
| Day 7 | $T_{max, D7}$ (h)* | 4.00 (2.50-8.00) | 2.00 (1.50-4.00) |
| | $C_{max, D7}$ (ng/mL) | 2086.968 ± 684.6861 | 2468.529 ± 747.0566 |
| | $AUC_{0-12, D7}$ (ng · h/mL) | 13178.286 ± 3929.9265 | 14879.645 ± 3363.7439 |
| | $C_{av, D7}$ (ng/mL) | 1098.190 ± 327.4939 | 1239.970 ± 280.3120 |
| | $C_{min, D7}$ (ng/mL) | 569.564 ± 196.7133 | 508.100 ± 113.1697 |
| | $C_{trough, D7}$ (ng/mL) | 582.824 ± 218.4362 | 516.784 ± 107.8804 |
| | $\lambda_{Z, D7}$ (h$^{-1}$) | 0.085 ± 0.0148 | 0.080 ± 0.0204 |
| | $t_{1/2, D7}$ (h) | 8.437 ± 1.5356 | 9.377 ± 3.3112 |
| | % Fluctuation,$_{D7}$ | 137.808 ± 27.6395 | 155.579 ± 27.9694 |
| | % Swing,$_{D7}$ | 279.625 ± 99.2218 | 395.274 ± 150.1218 |

TABLE 24

| | | Mean ± SD (untransformed data) | |
|---|---|---|---|
| Day | Parameters (Units) | Test Treatment (N = 19) | Reference Treatment (N = 19) |
| Day 1 | $T_{max, D1}$ (h)* | 5.00 (3.50-10.00) | 4.00 (2.50-5.05) |
| | $C_{max, D1}$ (ng/mL) | 301.468 ± 99.7215 | 801.742 ± 273.1573 |
| | $AUC_{0-12, D1}$ (ng · h/mL) | 1561.687 ± 450.3979 | 4501.058 ± 1393.8031 |
| | $\lambda_{Z, D1}$ (h$^{-1}$) | 0.181 ± 0.0687 | 0.165 ± 0.0552 |
| | $t_{1/2, D1}$ (h) | 4.467 ± 1.9011 | 4.891 ± 2.3143 |
| Day 7 | $T_{max, D7}$ (h)* | 5.00 (3.50-8.00) | 4.00 (2.50-6.00) |
| | $C_{max, D7}$ (ng/mL) | 326.616 ± 117.8864 | 1028.828 ± 550.2233 |
| | $AUC_{0-12, D7}$ (ng · h/mL) | 1926.863 ± 758.4068 | 6254.998 ± 2434.3707 |
| | $C_{av, D7}$ (ng/mL) | 160.572 ± 63.2006 | 521.250 ± 202.8642 |
| | $C_{min, D7}$ (ng/mL) | 77.147 ± 45.9512 | 259.338 ± 159.6484 |
| | $C_{trough, D7}$ (ng/mL) | 96.084 ± 48.7142 | 308.641 ± 168.2967 |
| | $\lambda_{Z, D7}$ (h$^{-1}$) | 0.086 ± 0.0250 | 0.086 ± 0.0248 |
| | $t_{1/2, D7}$ (h) | 8.746 ± 2.4298 | 8.881 ± 2.9696 |
| | % Fluctuation,$_{D7}$ | 162.696 ± 46.5619 | 151.932 ± 72.2780 |
| | % Swing,$_{D7}$ | 408.389 ± 200.0599 | 374.791 ± 251.9866 |

Figure 1:
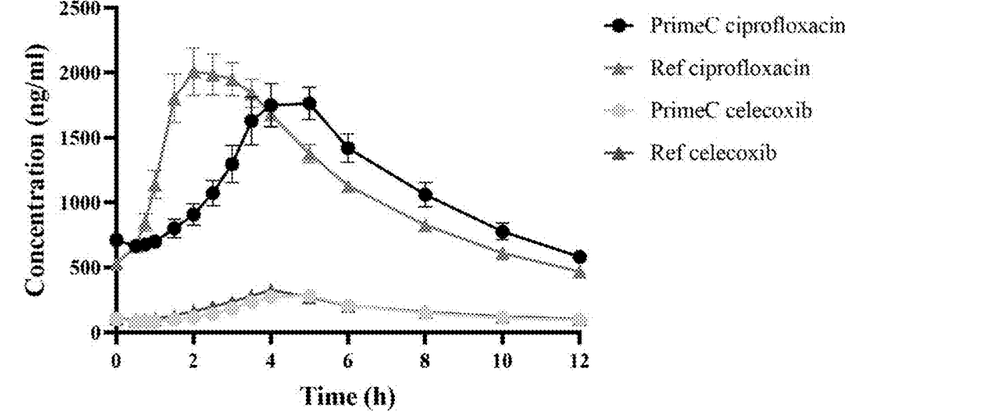
FIG. 1 depicts a graph showing normalized mean plasma concentration over time after administration of ciprofloxacin and celecoxib on the 7th day of administration to healthy volunteers, comparing administration via a combination tablet comprising ciprofloxacin and celecoxib (PrimeC) versus reference tablets (Ret).

FIG. 1 illustrates the mean plasma concentrations of both ciprofloxacin and celecoxib in the volunteers after the seventh day of administration. As the dosages for the group receiving the ERPC (designated PrimeC) and the reference tablets differ in dosage, the concentrations in the graph are normalized in that ciprofloxacin reference concentrations were multiplied by (680/750)=0.906667, and celecoxib reference concentrations were multiplied by (68/200)=0.34. The upper lines represent ciprofloxacin concentration after administration and the lower lines represent celecoxib. The ERPC group concentrations are represented by circles, and the reference group concentrations are represented by triangles.

As can be seen in the above tables and in FIG. 1, when comparing $T_{max}$ values for celecoxib and ciprofloxacin at Day 7 after the administration of the test treatment, once the test product has been administered for a number of days and steady state is reached, the values are $T_{max}$ for celecoxib (5 hours) is within the range of between 80% and 125% of the $T_{max}$ for ciprofloxacin (4 hours). This is evident in the peaks of concentration of ciprofloxacin and celecoxib occurring relatively at the same time in FIG. 1. However, when comparing $T_{max}$ values for celecoxib and ciprofloxacin at Day 7 after the administration of the reference treatment, the $T_{max}$ value for celecoxib is 200% of the $T_{max}$ value of ciprofloxacin. This is evident in the peaks of concentration for the ciprofloxacin reference product occurring earlier than the peak of concentration for the celecoxib reference product.

Described herein, according to an embodiment, is a tablet comprising celecoxib and ciprofloxacin or a pharmaceutically acceptable salt thereof, and low viscosity hydroxypropyl methylcellulose having a viscosity of between 2 cP and 150 cP, when measured as a 2% solution in water at 20° C. Optionally, the pharmaceutically acceptable salt of ciprofloxacin is ciprofloxacin HCl. Optionally, the hydroxypropyl methylcellulose has methoxyl substitution of between 28.0% and 30.0% and hydroxypropoxyl substitution of between 7.0% and 12.0%. Optionally, the hydroxypropyl methylcellulose has methoxyl substitution of between 19.0% and 24.0%, and hydroxypropoxyl substitution of between 7.0% and 12.0%. Optionally, the hydroxypropyl methylcellulose is present in an amount of between 3% and 10% by weight of the tablet. Optionally, hydroxypropyl methylcellulose is present in an amount of 5% by weight of the tablet. Optionally, the hydroxypropyl methylcellulose is present in an amount of between 4% and 15% by weight relative to the weight of the active ingredients, celecoxib and a pharmaceutically acceptable salt of ciprofloxacin, in the tablet. Optionally, the hydroxypropyl methylcellulose is present in an amount of between 6% and 8% by weight relative to the weight of the active ingredients. Optionally, the tablet comprises an extragranular component and an intragranular component, wherein the hydroxypropyl methylcellulose is present in the extragranular component. Optionally, the celecoxib and the pharmaceutically acceptable salt of ciprofloxacin are present in the intragranular component. Optionally, the tablet further comprises a filler, selected from the group consisting of soluble, non soluble and a mixture of soluble and non soluble fillers. Optionally, the filler is selected from the group consisting of: dicalcium phosphate, starch, pregelatinized starch, powdered cellulose, microcrystalline cellulose, mannitol, sucrose, sorbitol, and lactose. Optionally, the filler is microcrystalline cellulose, lactose, mannitol, or a combination thereof. Optionally, the low viscosity hydroxypropyl methylcellulose has a viscosity of 50 cP, when measured as a 2% solution in water at 20° C. Optionally, the ratio of weight of celecoxib to the weight of the ciprofloxacin free base is between 1:1 to 1:100. Optionally, the ratio of weight of celecoxib to the weight of the ciprofloxacin free base is 1:10-1:25. Optionally, the ratio of weight of celecoxib to the weight of the ciprofloxacin free base is 1:10. Optionally, the dissolution of ciprofloxacin is less than 70% and greater than 40%, within two hours, when placed in 750 ml of 0.1N HCl, in a Type II apparatus, at 75 revolutions per minute (RPM), and wherein the dissolution of ciprofloxacin is a total of at least 80% within 6 hours when placed in 750 ml of 0.1N HCl, in a Type II apparatus, at 75 RPM, 37° C. then after two hours, medium is modified to form phosphate buffer at pH of 6.8, comprising 1% SLS. Optionally, the dissolution of celecoxib is less than 80% within 6 hours and at least 80% within 12 hours when placed in 750 ml of 0.1N HCl, in a Type II apparatus, at 75 RPM, 37° C. then after two hours, medium is modified to form phosphate buffer at pH of 6.8, comprising 1% SLS. Optionally, more than 45% of both ciprofloxacin and celecoxib is released at 3 hours, and less than 90% is released at 6 hours, when placed in 750 ml of 0.1N HCl, in a Type II apparatus, at 75 RPM, 37° C. then after two hours, medium is modified to form phosphate buffer at pH of 6.8, comprising 1% SLS. Optionally, between 10% and 30% ciprofloxacin and celecoxib is released at 1 hour, and between 30% and 70% ciprofloxacin and celecoxib is released at 4 hours, and more than 85% ciprofloxacin and celecoxib is released at 12 hours, when placed in 900 ml of acetate buffer pH 4.5, in a Type II apparatus, at 75 RPM, 37° C. comprising 1% SLS. Optionally, upon administering the tablet to a human subject for 7 days with food and water, the Tmax for celecoxib in the subject's serum is within the range of between 80% and 125% of the Tmax for ciprofloxacin in the subject's serum.

Further described herein is a process for manufacture of the tablet comprising: forming granules comprising celecoxib and ciprofloxacin or a pharmaceutically acceptable salt thereof; adding a low viscosity hydroxypropyl methylcellulose having a viscosity of less than 150 cP, when measured as a 2% solution in water at 20° C. to the granules, to form a mixture; and compressing the mixture to form a tablet.

Further described herein is a method for treatment of amyotrophic lateral sclerosis (ALS) in a patient in need thereof, comprising administering to the patient a tablet described above.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A tablet comprising celecoxib and ciprofloxacin or a pharmaceutically acceptable salt thereof, and low viscosity hydroxypropyl methylcellulose having a viscosity of between 2 cP and 150 cP, when measured as a 2% solution in water at 20° C.

2. The tablet according to claim 1 wherein the pharmaceutically acceptable salt of ciprofloxacin is ciprofloxacin HCl.

3. The tablet according to claim 1 wherein the hydroxypropyl methylcellulose has methoxyl substitution of between 28.0% and 30.0% and hydroxypropoxyl substitution of between 7.0% and 12.0%.

4. The tablet according to claim 1 wherein the hydroxypropyl methylcellulose has methoxyl substitution of between 19.0% and 24.0%, and hydroxypropoxyl substitution of between 7.0% and 12.0%.

5. The tablet according to claim 1 wherein the hydroxypropyl methylcellulose is present in an amount of between 3% and 10% by weight of the tablet.

6. The tablet according to claim 5 wherein the hydroxypropyl methylcellulose is present in an amount of 5% by weight of the tablet.

7. The tablet according to claim 1 wherein the hydroxypropyl methylcellulose is present in an amount of between 4% and 15% by weight relative to the weight of the active ingredients, celecoxib and a pharmaceutically acceptable salt of ciprofloxacin, in the tablet.

8. The tablet according to claim 7 wherein the hydroxypropyl methylcellulose is present in an amount of between 6% and 8% by weight relative to the weight of the active ingredients.

9. The tablet according to claim 1 wherein the tablet comprises an extragranular component and an intragranular component, wherein the hydroxypropyl methylcellulose is present in the extragranular component.

10. The tablet according to claim 9 wherein the celecoxib and the pharmaceutically acceptable salt of ciprofloxacin are present in the intragranular component.

11. The tablet according to claim 1, and further comprising a filler, selected from the group consisting of soluble, non soluble and a mixture of soluble and non soluble fillers.

12. The tablet according to claim 11 wherein the filler is microcrystalline cellulose, lactose, mannitol, or a combination thereof.

13. The tablet according to claim 1 wherein low viscosity hydroxypropyl methylcellulose has a viscosity of 50 cP, when measured as a 2% solution in water at 20° C.

14. The tablet according to claim 1 wherein the ratio of weight of celecoxib to the weight of the ciprofloxacin free base is between 1:1 to 1:100.

15. The tablet according to claim 14 wherein the ratio of weight of celecoxib to the weight of the ciprofloxacin free base is 1:10-1:25.

16. The tablet according to claim 15 wherein the ratio of weight of celecoxib to the weight of the ciprofloxacin free base is 1:10.

17. The tablet according to claim 1 wherein between 10% and 30% ciprofloxacin and celecoxib is released at 1 hour, and between 30% and 70% ciprofloxacin and celecoxib is released at 4 hours, and more than 85% ciprofloxacin and celecoxib is released at 12 hours, when placed in 900 ml of acetate buffer pH 4.5, in a Type II apparatus, at 75 RPM, 37° C. comprising 1% SLS.

18. The tablet according to claim 1 wherein upon administering the tablet to a human subject for 7 days with food and water, the $T_{max}$ for celecoxib in the subject's serum is within the range of between 80% and 125% of the $T_{max}$ for ciprofloxacin in the subject's serum.

19. A process for manufacture of the tablet according to claim 1 comprising:
   a. forming granules comprising celecoxib and ciprofloxacin or a pharmaceutically acceptable salt thereof;
   b. adding a low viscosity hydroxypropyl methylcellulose having a viscosity of less than 150 cP, when measured as a 2% solution in water at 20° C. to the granules, to form a mixture; and
   c. compressing the mixture to form a tablet.

20. A method for treatment of amyotrophic lateral sclerosis (ALS) in a patient in need thereof, comprising administering to the patient a tablet according to claim 1.

* * * * *